(12) United States Patent
Darzynkiewicz et al.

(10) Patent No.: US 7,074,596 B2
(45) Date of Patent: Jul. 11, 2006

(54) SYNTHESIS AND USE OF ANTI-REVERSE MRNA CAP ANALOGUES

(75) Inventors: Edward Darzynkiewicz, Warsaw (PL); Robert E. Rhoads, Shreveport, LA (US); Janusz Stepinski, Warsaw (PL)

(73) Assignee: Board of Supervisors of Louisiana State University And Agricultural and Mechanical College, Shreveport, LA (US)

( * ) Notice: Subject to any disclaimer, the term of this patent is extended or adjusted under 35 U.S.C. 154(b) by 399 days.

(21) Appl. No.: 10/150,718

(22) Filed: May 17, 2002

(65) Prior Publication Data

US 2003/0194759 A1 Oct. 16, 2003

Related U.S. Application Data

(60) Provisional application No. 60/367,404, filed on Mar. 25, 2002.

(51) Int. Cl.
*C12P 19/36* (2006.01)
*C12P 19/34* (2006.01)
*C12Q 1/68* (2006.01)
*C12Q 1/70* (2006.01)
*C07H 21/02* (2006.01)

(52) U.S. Cl. .................. 435/90; 435/5; 435/6; 435/91; 435/91.1; 435/91.51; 536/23.1; 536/23.2; 536/25.4

(58) Field of Classification Search ............... 435/5, 435/6, 90, 91, 91.1, 91.51; 536/23.1, 23.2, 536/25.4
See application file for complete search history.

(56) References Cited

OTHER PUBLICATIONS

Nasahara et al Biochemical Journal "Crystal structures of 7-methylguanosine 5'-triphosphphosphate" vol. 362 pp. 539-544 (2002).*
CAPLUS ABS 2004-2239 of Ref U.*
Peng et al "Synthesis and Application of a Chain-Terminating Dinucleotide mRNA Cap Analog" Org Lett 4(2) 161-164 Dec. 20, 2001.*
Both, G. et al., "Methylation-dependent translation of viral messenger RNAs in vitro," *Proc. Natl. Acad. Sci. USA*, vol. 72, pp. 1189-1193 (1975).
Chu, L. et al., "Paradoxical observations on the 5' terminus of ovalbumin messenger ribonucleic acid," *J. Biol. Chem.*, vol. 253, pp. 5228-5231 (1978).
Contreras, R. et al., "Simple, efficient in vitro synthesis of capped RNA useful for direct expression of cloned eukaryotic genes," *Nucl. Acids Res.*, vol. 10, pp. 6353-6362 (1982).
Darzynkiewicz, E. et al., "β-Globin mRNAs capped with $m^7G$, $m_2^{2,7}G$ or $m_3^{2,2,7}G$ differ in intrinsic translation efficiency," *Nucl. Acids Res.*, vol. 16, pp. 8953-8962 (1988).

Darzynkiewicz, E. et al., "Chemical synthesis and characterization of 7-methylguanosine cap analogues," *Biochem.*, vol. 24, pp. 1701-1707 (1985).
Darzynkiewicz, E. et al., "Inhibition of eukaryotic translation by nucleoside 5'-monophosphate analogues of mRNA 5'-cap: Changes in N7 substituent affect analogue activity," *Biochem.*, vol. 28, pp. 4771-4778 (1989).
Darzynkiewicz, E. et al., "New 'anti-reverse' 5'-mRNA dinucleotide cap analogues (ARCA)," Abstract POTH-035, 27th Meeting of the Federation of European Biochemical Societies (Lisbon, Portugal, Jun. 30-Jul. 5, 2001).
Edery, I. et al., "Cap-dependent RNA splicing in a HeLa nuclear extract," *Proc. Natl. Acad. Sci. USA*, vol. 82, pp. 7590-7594 (1985).
Kadokura, M. et al. 1997, "Efficient synthesis of γ-methyl-capped guanosine 5'-triphosphate as a 5'-terminal unique structure of U6 RNA via a new triphosphate bond formation involving activation of methyl phosphorimidazolidate using $ZnCl_2$ as a catalyst in DMF under anhydrous conditions," *Tetrahedron Lett.*, vol. 38, pp. 8359-8362 (1997).
Konarska, M. et al., Recognition of cap structure in splicing in vitro of mRNA precursors. *Cell*, vol. 38, pp. 731-736 (1984).
Melton, D. et al., "Efficient in vitro synthesis of biologically active RNA and RNA hybridization probes from plasmids containing a bacteriophage SP6 promoter," *Nucl. Acids Res.*, vol. 12, pp. 7035-7056 (1984).
Muthukrishnan, S. et al., "5'-Terminal 7-methylguanosine in eukaryotic mRNA is required for translation," *Nature*, vol. 255, pp. 33-37 (1975).
Pasquinelli, A. et al., "Reverse 5'caps in RNAs made in vitro by phage RNA polymerases," *RNA*, vol. 1, pp. 957-967 (1995).

(Continued)

*Primary Examiner*—Herbert J. Lilling
(74) *Attorney, Agent, or Firm*—John H. Runnels

(57) ABSTRACT

The ability to synthesize capped RNA transcripts in vitro has been of considerable value in a variety of applications. However, one-third to one-half of the caps have, until now, been incorporated in the reverse orientation. Such reverse caps impair the translation of in vitro-synthesized mRNAs. Novel cap analogues, such as $P^1$-3'-deoxy-7-methylguanosine-5'$P^3$-guanosine-5'triphosphate and $P^1$-3'-O,7-dimethylguanosine-5'$P^3$-guanosine-5'triphosphate, have been designed that are incapable of being incorporated into RNA in the reverse orientation. Transcripts produced with SP6 polymerase using "anti-reverse" cap analogues were of the predicted length. Analysis of the transcripts indicated that reverse caps were not formed. The in vitro translational efficiency of transcripts with the novel "anti-reverse" cap analogues was significantly higher than that of transcripts formed with conventional caps.

12 Claims, 4 Drawing Sheets

OTHER PUBLICATIONS

Peng, Z. et al., "Synthesis and application of a chain-terminating dinucleotide mRNA cap analog," *Org. Lett.*, vol. 4, pp. 161-164 (2002), published on the Web, Dec. 2001.

Sanger, F. et al., "DNA sequencing with chain-terminating inhibitors," *Proc. Natl. Acad. Sci. USA*, vol. 74, pp. 5463-5467 (1977).

Stepinski, J. et al., "Synthesis and properties of mRNAs containing the novel 'anti-reverse' cap analogs 7-methyl(3'-O-methyl)GpppG and 7-methyl(3'-deoxy)GpppG," *RNA*, vol. 7, pp. 1486-1495 (2001).

Stepinski, J. et al., "Synthesis and properties of 'anti-reverse' cap analogues," Abstract, 6th Meeting of the RNA Society (Banff, Canada, May 29-Jun. 3, 2001).

Stepinski, J. et al., "Preparation and properties of mRNAs capped with the novel 'anti-reverse' dinucleotide cap analogues," Abstract P-13, 4th West Coast Meeting on mRNA Stability and Translation (Seattle, WA, Oct. 14-16, 2001).

Yisraeli, J. et al., Synthesis of long, capped transcripts in vitro by SP6 and T7 RNA polymerases, pp. 42-50 in J. Dahlberg et al. (Eds.), *Meth. Enzymol.*, vol. 180., pp. 42-50 (1989).

* cited by examiner

SYNTHESIS AND USE OF ANTI-REVERSE MRNA CAP ANALOGUES

The benefit of the Mar. 25, 2002 filing date of provisional patent application Ser. No. 60/367,404 is claimed under 35 U.S.C. § 119(e).

The development of this invention was partially funded by the United States Government under grant number GM20818 awarded by the National Institutes of Health. The United States Government has certain rights in this invention. The development of this invention was partially funded by the Government of Poland under grant number 6 P04A 055 17 awarded by the Polish Committee for Scientific Research (KBN).

In eukaryotes, the 5' end of most mRNA is blocked, or "capped." In addition, there are some other forms of RNA that are also capped. The cap contains a 5'—5' triphosphate linkage between two nucleotides, and also contains methyl groups. The capping of RNA promotes its normal function in cells.

The ability to synthesize capped RNA molecules in vitro is therefore useful, because it allows workers to prepare RNA molecules that behave properly as mRNA transcripts in a variety of in vitro applications. Such applications include both research applications and commercial production of certain polypeptides in an in vitro translation system, for example the production of polypeptides containing an "unnatural" amino acid at a specific site.

The method most frequently used to make capped RNAs in vitro is to transcribe a DNA template with either a bacterial RNA polymerase or a bacteriophage RNA polymerase in the presence of all four ribonucleoside triphosphates and a cap dinucleotide such as $m^7G(5')ppp(5')G$. The polymerase initiates transcription with a nucleophilic attack by the 3'-OH of the Guo moiety in $m^7GpppG$ on the α-phosphate of the next templated nucleoside triphosphate, resulting in the initial product $m^7GpppGpN$. The alternative, GTP-initiated product pppGpN is suppressed by setting the ratio of $m^7GpppG$ to GTP between 5 and 10 in the transcription reaction mixture.

Synthetic RNAs may be synthesized by cell-free transcription of DNA templates. See R. Contreras et al., "Simple, efficient in vitro synthesis of capped RNA useful for direct expression of cloned eukaryotic genes," Nucl. Acids Res., vol. 10, pp. 6353–6362 (1982); J. Yisraeli et al., "Synthesis of long, capped transcripts in vitro by SP6 and T7 RNA polymerases", pp.42–50 in J. Dahlberg et al. (Eds.), Meth. Enzymol., vol. 180., pp.42–50 (1989); and D. Melton et al, "Efficient in vitro synthesis of biologically active RNA and RNA hybridization probes from plasmids containing a bacteriophage SP6 promoter," Nucl. Acids Res., vol.12, pp. 7035–7056 (1984).

Capped RNAs thus produced are active in in vitro splicing reactions. See M. Konarska et al., "Recognition of cap structure in splicing in vitro of mRNA precursors". Cell, vol. 38, pp. 731–736 (1984); and I. Edery et al., "Cap-dependent RNA splicing in a HeLa nuclear extract," Proc. Natl. Acad. Sci. USA, vol. 82, pp. 7590–7594 (1985).

Capped mRNAs are translated more efficiently than are non-capped mRNAs. See S. Muthukrishnan et al., "5'-Terminal 7-methylguanosine in eukaryotic mRNA is required for translation," Nature, vol. 255, pp. 33–37 (1975); L. Chu et al., "Paradoxical observations on the 5' terminus of ovalbumin messenger ribonucleic acid," J. Biol. Chem., vol. 253, pp. 5228–5231 (1978); E. Darzynkiewicz et al., "β-Globin mRNAs capped with $m^7G$, $m_2^{2,7}G$ or $m_3^{2,2,7}G$ differ in intrinsic translation efficiency," Nucl. Acids Res., vol. 16, pp. 8953–8962 (1988); and E. Darzynkiewicz et al., "Inhibition of eukaryotic translation by nucleoside 5'-monophosphate analogues of mRNA 5'-cap: Changes in N7 substituent affect analogue activity," Biochem., vol. 28, pp. 4771–4778 (1989).

5'-Unmethylated mRNAs have been reported to be translationally less active than 5'-methylated mRNAs. See G. Both et al., "Methylation-dependent translation of viral messenger RNAs in vitro," Proc. Natl. Acad. Sci. USA, vol. 72, pp. 1189–1193 (1975).

E. Darzynkiewicz et al., "Chemical synthesis and characterization of 7-methylguanosine cap analogues," Biochem., vol. 24, pp.1701–1707 (1985) reported the synthesis of derivatives of 7-methylguanosine 5'-phosphate that were modified in the ribose moiety by 2'-O or 3'-O-methylation, or by conversion to the 2'-deoxy or arabinosyl form, and reported that these derivatives retained cap analogue activity.

F. Sanger et al., "DNA sequencing with chain-terminating inhibitors," Proc. Natl. Acad. Sci. USA, vol. 74, pp. 5463–5467 (1977) reported a method for determining DNA nucleotide sequences with 2',3'-dideoxy and arabinonucleoside analogues of normal deoxynucleoside triphosphates, in which the analogs act as specific chain-terminating inhibitors of DNA polymerase.

M. Kadokura et al. 1997, "Efficient synthesis of γ-methyl-capped guanosine 5'-triphosphate as a 5'-terminal unique structure of U6 RNA via a new triphosphate bond formation involving activation of methyl phosphorimidazolidate using $ZnCl_2$ as a catalyst in DMF under anhydrous conditions," Tetrahedron Lett., vol. 38, pp. 8359–8362 (1997) reported the synthesis of $CH_3pppG$ from GDP and the imidazolide of methyl phosphate in DMF, obtaining a yield of 39% in the absence of $ZnCl_2$, and a yield of 98% in the presence of $ZnCl_2$.

A. Pasquinelli et al., "Reverse 5' caps in RNAs made in vitro by phage RNA polymerases," RNA, vol. 1, pp.957–967 (1995) reported that bacteriophage polymerases also use the 3'—OH of the 7-methylguanosine moiety of $m^7GpppG$ to initiate transcription, demonstrating that approximately one-third to one-half of RNA products made with this cap analogue actually contain the "reverse cap" $Gpppm^7GpN$. Such reverse-capped RNA molecules behave abnormally. The same authors reported that when reverse-capped pre-U1 RNA transcripts were injected into Xenopus laevis nuclei, they were exported more slowly than natural transcripts. Similarly, cytoplasmic reverse-capped U1 RNAs in the cytoplasm were not properly imported into the nucleus. The presence of a cap on mRNA strongly stimulates translation of an mRNA transcript into protein. To the knowledge of the present inventors, there have been no previous reports directly addressing whether, and at what rate, reverse-capped mRNAs are translated into protein. However, based on what is known about recognition of the cap structure by elF4E, one would expect reverse-capped mRNAs to be translated no more efficiently than uncapped RNAs.

Z. Peng et al., "Synthesis and application of a chain-terminating dinucleotide mRNA cap analog," Org. Lett., vol. 4, pp. 161–164 (2002; published on the Web, December 2001; and including the supporting information for this article as reprinted from the journal's web site) reported the synthesis of a chain-terminating mRNA cap dinucleotide, $3'-O-Me-m^7G(5')pppG$, and its use in the in vitro transcription of homogeneously capped RNA. Computer modeling was said to indicate that RNA capped with the compound would be a substrate for cap-dependent translation.

Because existing synthetically capped RNAs contain about one-third to one-half reverse caps, the overall translational activity of such a RNA preparation is reduced considerably. Other functional properties of the mRNA may also be affected. There is a previously unfilled need for a way to prepare capped RNA molecules in vitro, in which all or essentially all the caps have the proper orientation.

We have discovered and synthesized cap analogues that will not be incorporated into an mRNA molecule in the reverse orientation. In experiments in which we synthesized and tested two prototype "anti-reverse" cap analogues (AR-CAs), we found that both were exclusively incorporated into mRNA molecules in the correct orientation. Furthermore, both behaved like natural RNA caps in interactions with the translational machinery. The resulting mRNAs were considerably more active translationally than are traditional in vitro-prepared RNAs containing a mixture of caps in both the correct and the reversed orientations.

Transcription by bacteriophage RNA polymerases in the presence of $m^7GpppG$ is initiated with a nucleophilic attack by the 3'-OH of either the $m^7Guo$ moiety or of the Guo moiety on the electrophilic α-phosphate of the first templated nucleoside triphosphate. We eliminated one of these two 3'-OH groups, so that the nucleophilic attack would cause incorporation only in the correct orientation. We have made two prototype ARCAs. In the case of $P^1$-3'-deoxy-7-methylguanosine-5'$P^3$-guanosine-5'triphosphate (FIG. 1, Compound 9, henceforth abbreviated $m^73'dGpppG$), we substituted an —H for the 3'-OH. In the case of $P^1$-3'-O,7-dimethylguanosine-5'$P^3$-guanosine-5'triphosphate (FIG. 1, compound 10, henceforth abbreviated $m_2^{7,O3'}GpppG$), we instead substituted a —$OCH_3$ for the 3'-OH.

We also developed new coupling strategies to synthesize the prototype ARCAs. To avoid preparing imidazole derivatives from 7-methylated substrates, the activation of which can be difficult, we developed a new coupling strategy involving guanosine 5'-phosphorimidazolide and the modified 7-methylated nucleoside diphosphate. We obtained high yields by conducting the coupling reaction in the presence of $ZnCl_2$ instead of $Mn^{2+}$, and by using anhydrous dimethylformamide (DMF) instead of water as a solvent. See FIG. 1, depicting schematically the synthesis of "anti-reverse" cap analogs. (In FIG. 1, "ImGMP" refers to guanosine 5'-imidazolide monophosphate.)

MATERIALS AND METHODS

Synthesis of Mono- and Dinucleotides

EXAMPLE 1

Figure 1:
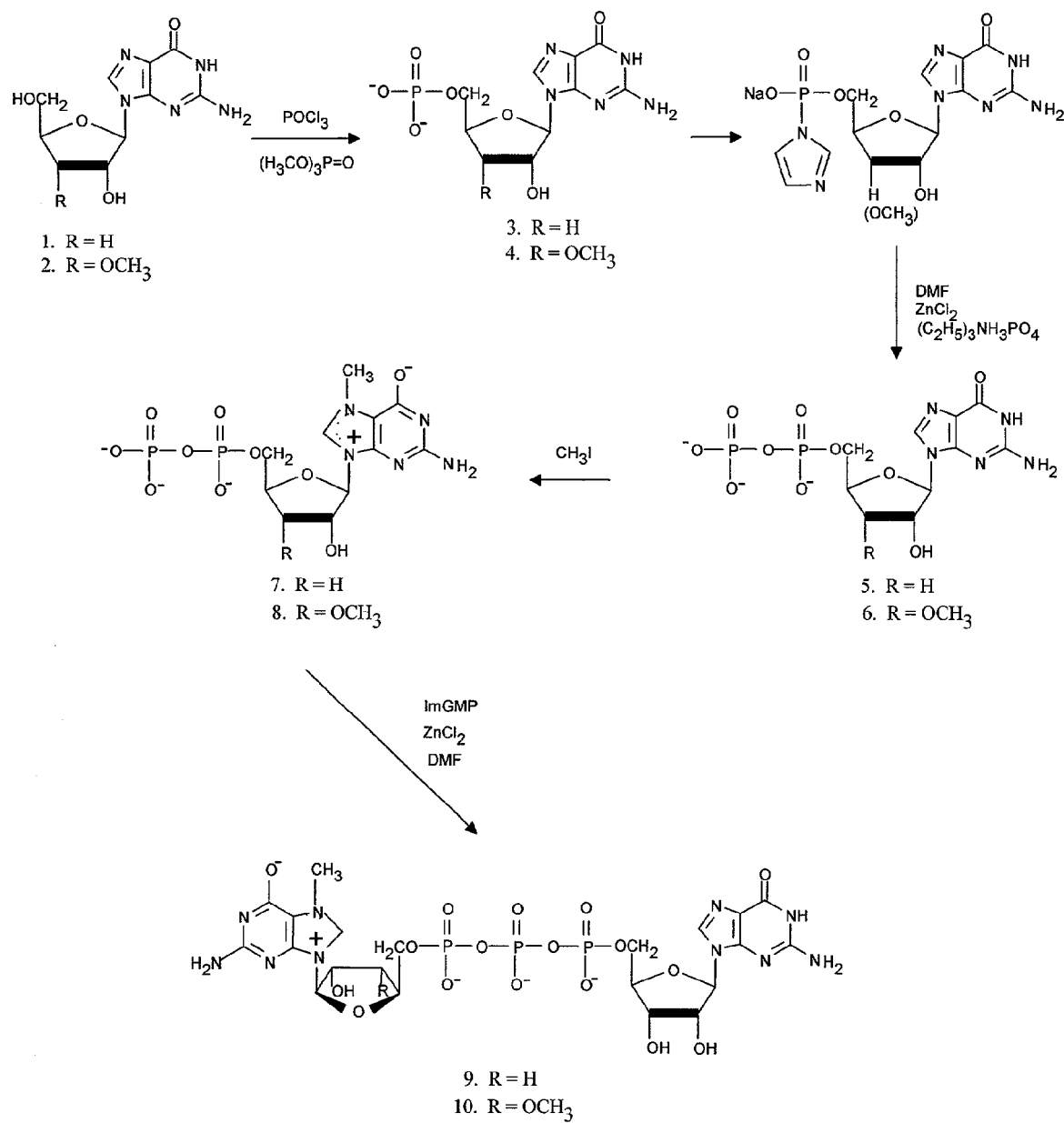
FIG. 1 depicts the synthesis of "anti-reverse" cap analogs.

3'-Deoxyguanosine 5'-monophosphate (Compound 3). 3'-Deoxyguanosine (Compound 1, commercial product from Sigma, 50 mg, 0.19 mmol) was stirred overnight with trimethylphosphate (2 mL) and phosphorus oxychloride (53 μL, 0.57 mmol) at 6° C. The reaction was quenched by adding 20 mL of water and neutralizing with 1 M $NaHCO_3$. DEAE-Sephadex chromatography using a linear gradient of 0–0.9 M TEAB afforded Compound 3 (yield: 45 mg, 43%).

EXAMPLE 2

3'-O-Methylguanosine 5'-monophosphate (Compound 4) was obtained by a procedure analogous to that for Compound 3, but instead starting with 59 mg of 3'-O-methylguanosine (Compound 2), which was prepared by the method of J. Kusmierek et al., "A new route to 2'(3')-O-alkyl purine nucleosides," *Nucl. Acids Res. Special Publ. No. 4*, pp. s73–s77 (1978) (yield: 80 mg, 69%).

EXAMPLE 3

3'-Deoxyguanosine 5'-diphosphate (Compound 5). Compound 3 (55 mg, TEA salt, 0.1 mmol), imidazole (34 mg, 0.5 mmol) and 2,2'-dithiodipyridine (Aldrich, 44 mg, 0.2 mmol) were mixed in anhydrous DMF (1.2 mL) and TEA (14 μL). Triphenylphosphine (52 mg, 0.2 mmol) was added, and the mixture was stirred for 5 h at room temperature. The mixture was placed in a centrifuge tube, and sodium perchlorate (49 mg, anhydrous) dissolved in acetone (6 mL) was added. After cooling for 2 h in a refrigerator, the mixture was centrifuged and the supernatant was discarded. The precipitate was ground with a new portion of acetone, cooled and centrifuged again. The process was repeated once more, and the precipitate was dried in a vacuum desiccator over $P_4O_{10}$. The imidazolide thus obtained was dissolved in 1.2 mL of DMF, and 200 mg of triethylammonium phosphate was added. (The latter was prepared from TEA and phosphoric acid followed by drying over $P_4O_{10}$ in a desiccator to obtain a semicrystalline mass.) Finally, 80 mg of $ZnCl_2$ were added, and the reaction mixture was stirred at room temperature for 6.5 h, poured into a beaker containing a solution of 250 mg EDTA in 15 mL water, and neutralized with 1 M $NaHCO_3$. Chromatographic isolation on a DEAE-Sephadex column using a linear gradient of 0–1 M TEAB gave Compound 5 (yield: 41 mg, 66%).

EXAMPLE 4

3'-O-Methylguanosine 5'-diphosphate (Compound 6) was obtained by a procedure analogous to that for Compound 5, except starting from 58 mg of Compound 4 (yield: 32 mg, 49%).

EXAMPLE 5

3'-Deoxy-7-methylguanosine 5'-diphosphate (Compound 7). Compound 5 (34 mg, 0.055 mmol) was mixed with 1 mL of dimethylsulfoxide, 1 mL of DMF, and 100 μL of methyl iodide at room temperature. After 3 h the reaction mixture was treated with 30 mL of cold water and extracted three times with 10-mL portions of diethyl ether. After neutralization with $NaHCO_3$, chromatographic separation of the aqueous phase on DEAE-Sephadex, using a linear gradient of 0 to 0.8 M TEAB, gave Compound 7 (yield: 10 mg, 28%).

EXAMPLE 6

3'-O, 7-Dimethylguanosine 5'-diphosphate (Compound 8) was obtained by a procedure analogous to that for Compound 7, except that the starting material was 66 mg of Compound 6 (yield: 64 mg, 95%).

EXAMPLE 7

P¹-3'-Deoxy-7-methylguanosine-5' P³-guanosine-5'triphosphate (Compound 9). GMP (purchased from Sigma, converted to the TEA salt, 29 mg, 0.05 mmol), imidazole (17 mg, 0.25 mmol), and 2,2'-dithiodipyridine (22 mg, 0.1 mmol, purchased from Aldrich) were mixed in anhydrous DMF (1.2 mL) and TEA (7 µL). Triphenylphosphine (26 mg, 0.1 mmol) was added, and the mixture was stirred for 5 h at room temperature. The mixture was placed in a centrifuge tube, and sodium perchlorate (25 mg, anhydrous) dissolved in acetone (6 mL) was added. The procedure for washing the precipitate with acetone and drying over $P_4O_{10}$ was the same as for Compound 5. The imidazolide of GMP thus obtained was dissolved in DMF (1.2 mL), and Compound 7 (10 mg, TEA salt, 0.015 mmol) was added. Next $ZnCl_2$ (40 mg) was added. The mixture was stirred at room temperature overnight, poured into a beaker containing a solution of 125 mg of EDTA in 15 mL of water, and neutralized with 1 M $NaHCO_3$. Chromatographic isolation as for Compound 5 gave Compound 9 (13 mg, 88% based on the amount of Compound 7 used).

EXAMPLE 8

P¹-3'-O, 7-Dimethylguanosine-5'P³-guanosine-5'triphosphate (Compound 10) was prepared from GMP and Compound 8 (34 mg) by a procedure analogous to that for Compound 9 (yield: 23 mg, 78%).

EXAMPLES 9 & 10

The final products (Compounds 9 and 10) were converted to their Na⁺ salts by ion exchange on a small column of Dowex 50W×8 (Na⁺ form), followed by evaporation of the eluates to a small volume, precipitation with ethanol, and centrifugation to give amorphous white powders. Parameters from the ¹H NMR spectra of Compounds 9 and 10 are shown in Tables 1 and 2 below.

EXAMPLE 11

7-Methylguanosine 3',5'-diphosphate. Guanosine 3',5'-diphosphate was methylated to make the chromatographic standard pm⁷Gp (FIG. 2) by the same procedure as used for Compound 7.

EXAMPLE 12

Column Chromatography

Both final products (Compounds 9 and 10, FIG. 1) and intermediate nucleotides (Compounds 3–8) were isolated from reaction mixtures by column chromatography on DEAE-Sephadex (A-25, $HCO_3^-$ form) using a linear gradient of triethylammonium bicarbonate (TEAB), pH 7.5, in water. Fractions were collected, and products peaks (monitored at 260 nm) were pooled and evaporated to dryness, with ethanol added repeatedly to remove the TEAB buffer. The products were obtained as TEA salts.

The purity of intermediates and products was monitored at 260 nm by analytical HPLC using a Spectra-Physics SP8800 apparatus on a 25-cm LC-18-T reverse phase column (Supelco). The mobile phase was a linear gradient of methanol from 0 to 25% in 0.1 M $KH_2PO_4$, pH 6, over 15 min with flow rate of 1.3 mL/min.

Mono- and dinucleotides obtained by enzymatic digestion of in vitro-synthesized RNAs were analyzed by HPLC using a Waters 625 instrument with a 996 PDA detector on a 4.5×250 mm Partisil 10SAX/25 column (Whatman). The program for elution of nucleotides comprised water for the first 5 min; a linear gradient of 87.5 to 500 mM $KH_2PO_4$, pH 3.5, over 35 min; a linear gradient of 87.5 to 500 mM of $KH_2PO_4$ over 30 min; and isocratic elution at 500 mM $KH_2PO_4$ for 21 min—all at a flow rate of 1 mL/min.

EXAMPLE 13

Spectroscopy

¹H NMR and ¹³C NMR spectra were recorded on a Varian UNITY plus 500 MHz instrument in dimethylsulfoxide-$d_6$ (for nucleoside intermediates) or $D_2O$ (for mono- and dinucleotides). Absorption spectra were obtained on a Cary 3E spectrophotometer.

¹H NMR spectra for compounds 9 and 10 were run at 25° C. at 1.4 mg/0.7 mL and 0.4 mg/0.7 mL in $D_2O$, respectively. Conformations of the sugar moieties were derived from the vicinal ¹H—¹H coupling constants. Conformations of the phosphate groups were determined from the ¹H—³¹P coupling constants.

EXAMPLES 14 & 15

In vitro Synthesis of RNA

Two lengths of RNA, either uncapped or capped with one of the cap analogues, were synthesized by in vitro transcription. The DNA template used for both lengths of RNA was pSP–luc+ (Promega), which contains an SP6 bacteriophage promoter and a sequence encoding luciferase. To generate the short RNAs (43 bases exclusive of the cap), the plasmid was digested with NcoI. To generate the long RNAs (1706 bases, containing the entire luciferase coding region), the plasmid was digested with EcoRl. A typical 20 µL in vitro transcription reaction contained 40 mM Tris-HCl, pH 7.9, 6 mM $MgCl_2$, 2 mM spermidine, 10 mM DTT, 2 µg BSA, 20 units of RNasin (Promega), 0.5 mM ATP, 0.5 mM CTP, 0.5 mM UTP, 0.1 mM GTP, 1 mM cap analogue (GpppG, m7GpppG, m⁷3'dGpppG, or $m_2^{7,O3'}$GpppG), 0.2–1.0 µg DNA, and 20 units of SP6 polymerase (Promega). Reactions to synthesize the short RNAs also contained 28 µCi of [α-³²P]ATP (ICN), and those to synthesize the long RNAs contained 0.8 µCi of [α-³²P]CTP (ICN). Reaction mixtures were incubated for 60 min at 37° C., extracted with phenol and chloroform, and the solution was made 2 M in sodium acetate. The nucleic acids were then precipitated with 3 volumes of ethanol on dry ice for 5 min, and the mixture was centrifuged at 14,000 rpm for 30 min. The resulting pellet was dissolved in water, and the solution was made 0.2 M in sodium acetate. The nucleic acid was precipitated with 2.5 volumes of ethanol at 4° C. for 30 min, and the mixture was centrifuged at 14,000 rpm for 30 min. The pellet was allowed to air-dry and then dissolved in diethylpyrocarbonate-treated water.

EXAMPLE 16

Enzymatic Digestion of RNAs

The short RNAs were digested with 67 U RNase T2 (Life Technologies) in 15 µL of 0.14 M sodium acetate, pH 4.6, at 37° C. for 60 min. In some cases, the RNAs were subjected to a two-step digestion instead. The first digestion was with 10 U TAP (tobacco acid pyrophosphatase) (Epicentre Technologies) in 5 µL of 50 mM sodium acetate, pH 6.0, 1 mM EDTA, 0.1% β-mercaptoethanol, and 0.01% Triton X-100 at 37° C. for 60 min. The digestion was continued for 60 min at 37° C. with 67 U RNase T2 in a final volume of 16 μL of 0.12 M sodium acetate, pH 4.6. Samples were analyzed without further treatment by anion exchange HPLC as described above.

EXAMPLE 17

Cell-free Translation

A micrococcal nuclease-treated RRL (rabbit reticulocyte lysate) system was used for in vitro translation as described in A. Cai et al., "Quantitative assessment of mRNA cap analogs as inhibitors of in vitro translation," Biochemistry, vol.38, pp. 8538–8547 (1999). In some cases, the mRNA used in this system was natural rabbit globin mRNA, and protein synthesis was measured by incorporation of [$^3$H]Leu into a trichloroacetic acid-precipitable form. In other cases, the mRNA was luciferase mRNA (the long form), synthesized in vitro as described above, and protein synthesis was assayed by measuring luciferase activity using beetle luciferin (Promega) as a substrate, and a Monolite 2010 luminometer to measure light emission.

The ability of cap analogues to inhibit cell-free translation in the RRL system programmed with globin mRNA was measured as described in Cai et al. (1999). Data were fit by least squares minimization to a theoretical rate equation. The concentrations of cap analogue solutions were measured by UV absorption at pH 7.0 using the following parameters for $\lambda$ and $\epsilon_M$, respectively: GpppG, 251 nm, $25.5 \times 10^3$; m$^7$GpppG, m$^7$3'dGpppG, or m$_2^{7,O3'}$GpppG, 255 nm, $22.6 \times 10^3$.

RESULTS $^{13}$C NMR and UV spectra for intermediates were in good agreement with the predicted structures (data not shown). The $^1$H NMR assignments of protons in both prototype ARCAs confirmed their chemical structures (Table 1). Two sets of sugar $^1$H signals in each spectrum pointed to dinucleotides. The presence of methyl signals at 4.068 ppm (Compound 10) and 4.027 (Compound 9), together with disappearance of the H(8) resonances due to exchange for solvent deuterium, testified to the presence of 7-methylguanine. In the case of Compound 10, the additional methyl group was observed at 3.483 ppm, accompanied by a characteristic upfield shift of the H3' signal. Lack of the 3'-hydroxyl in Compound 9 gave the characteristic "deoxy" pattern of H3'/H3" at 2.086–2.148 ppm, with further scalar couplings to H4' and H2'.

TABLE 1

$^1$H NMR chemical shifts in ppm versus internal sodium 3-trimethylsilyl-[2,2,3,3-D$_4$]-propionate

| | m$^7$3'dGpppG (Compound 9) | | m$_2^{7, O3'}$GpppG (Compound 10) | |
|---|---|---|---|---|
| | m$^7$3'dG | G | m$_2^{7, O3'}$G | G |
| H8 | —[a] | 8.016 | —[a] | 7.990 |
| H1' | 5.796 | 5.776 | 5.864 | 5.785 |
| H2' | 4.587 | 4.650 | 4.682 | 4.687 |
| H3' | 2.148 | 4.473 | 4.109 | 4.473 |
| H3" | 2.086 | — | — | — |
| H4' | 4.728 | 4.346 | 4.428 | 4.339 |
| H5' | 4.460 | 4.26[b] | 4.384 | 4.278 |
| H5" | 4.196 | 4.26[b] | 4.219 | 4.239 |
| CH$_3$ | 4.027 | — | 4.068 (N7) 3.483 (3'O) | — |

[a] deuterated
[b] signal overlapping

Table 2 provides NMR information concerning conformational parameters. These data reflected populations of the N form in the N⇔S dynamic equilibrium of the sugar ring, populations of the +sc (gauche-gauche) conformer about C4'–C5', and populations of the ap (gauche'-gauche') conformer of the phosphate group. The 7-substituted Guo moieties showed the characteristic preference for the N conformer, up to 100% in the case of m$_2^{7,O3'}$Guo, as opposed to Guo, in which the S conformer dominates. The preference for +sc was also more pronounced in the 7-substituted guanosines. The conformation of the Guo moiety of ARCAs was similar to that of Guo in normal caps, in which about 64% has been reported to be in the S form (36% N) and about 63% in the +sc form. Thus, m$_2^{7,O3'}$Guo and m$^7$3'dG both displayed conformational features that were characteristic of m$^7$Guo rather than of Guo.

TABLE 2

$^1$H—$^1$H and $^1$H–$^{31}$P coupling constants in Hz (±0.2), and conformer populations (±5%) in the dynamic equilibria N ⇔ S of the sugar ring, and about C4'–C5' (% + sc) and C5'–O5' (% ap) bonds

| | m$^7$3'dGpppG (Compound 9) | | m$_2^{7, O3'}$GpppG (Compound 10) | |
|---|---|---|---|---|
| | m$^7$3'dG | G | m$_2^{7, O3'}$G | G |
| J(1',2') | 0.0[a] | 6.2 | 4.0 | 6.3 |
| J(2',3') | 4.5 | 5.2 | 5.0 | 5.1 |
| J(2',3") | 0.0[a] | — | — | — |
| J(3',3") | 14.2 | — | — | — |
| J(3',4') | 10.4 | 3.7 | 5.1 | 3.6 |
| J(3",4') | 5.1 | — | — | — |
| J(4',5') | 3.0[b] | 4.0[b] | 3.0 | 4.1 |
| J(4',5") | 2.7 | 4.0[b] | 2.6 | 4.2 |
| J(5',5") | 11.6 | b | 11.5 | 11.8 |
| J(5',P) | 5.0 | 6.0[b] | 4.4 | 5.4 |
| J(5",P) | 5.8 | 6.0[b] | 5.9 | 6.5 |
| J(4',P) | 1.0[b] | 1.0[b] | 1.0[b] | 1.0[b] |
| % N | 100 | 37 | 56 | 36 |
| % + sc[c] | 80 | 55[b] | 80 | 54 |
| % ap[d] | 72 | 66[b] | 74 | 66 |

[a] less than the line width, ~1 Hz
[b] approximate value
[c] +synclinal, i.e., O5' in gauche orientation to O4' and C3'
[d] antiperiplanar, i.e., P5' in trans orientation to C4'

EXAMPLE 18

Synthesis of ARCA-capped RNA Transcripts

We tested the prototype ARCAs in an in vitro transcription system. A template DNA was first generated by digesting the plasmid pSP–luc+ with EcoRl. The theoretical size of an RNA transcript from this template should be 1706 bases, which was consistent with the approximate size of the products that was observed by electrophoretic migration from reactions carried out in the presence of [α-$^{32}$P]ATP and either GpppG, m$^7$GpppG, m$^7$3'dGpppG, or m$_2^{7,O3'}$GpppG. (data not shown). Samples were run on a 1% agarose gel containing 0.12 M formaldehyde in 0.4 M 3-(N-morpholino) propanesulfonic acid, pH 7.0, 0.1 M sodium acetate, and 0.01 M EDTA at 70 mA for 5 h. A PhosphorImage was obtained with a Molecular Dynamics Storm 860 instrument. Standards used for comparison were rabbit 28S rRNA, 18S rRNA, and β-globin mRNA.

In six separate experiments, the yield of RNA product in the presence of ARCAs was not significantly different from the yield in the presence of m$^7$GpppG.

EXAMPLE 19

Analysis of Cap Orientation in ARCA-Capped RNA Transcripts

The structure of the ARCAs was designed to prevent incorporation into RNA in the reverse orientation. We verified this property experimentally by digesting RNAs capped with ARCAs with RNase T2 and TAP. To obtain a higher proportion of radioactivity in the cap versus the internal positions, a shorter DNA template was produced by cleaving pSP–luc+ with NcoI instead of EcoRI. This digestion was expected to yield an RNA product of 43 bases (plus the cap). The size of this product was confirmed by polyacrylamide gel electrophoresis in Tris/borate/EDTA/urea (data not shown).

RNase T2 digests RNA with no base specificity. Thus, it was expected to generate primarily 3'-NMPs from this RNA. Those nucleotide residues that were located 5' to an A residue would acquire a $^{32}$P-labeled 3'-phosphate by nearest-neighbor transfer. The pyrophosphate bonds in the cap, however, are not susceptible to RNase T2. Since the first nucleotide residue after the cap in the synthetic RNA is an A, the α-phosphate of [α-$^{32}$P]ATP would be transferred to the cap following RNase T2 digestion. Thus, for RNAs initiated in the normal orientation with m$^7$GpppG, the product was m$^7$GpppGp* (where p* denotes radioactive $^{32}$p). The RNase T2-digestion products expected from RNAs initiated with GTP or with the four cap analogues in either normal or reverse orientations are shown in Table 3.

Figure 2:
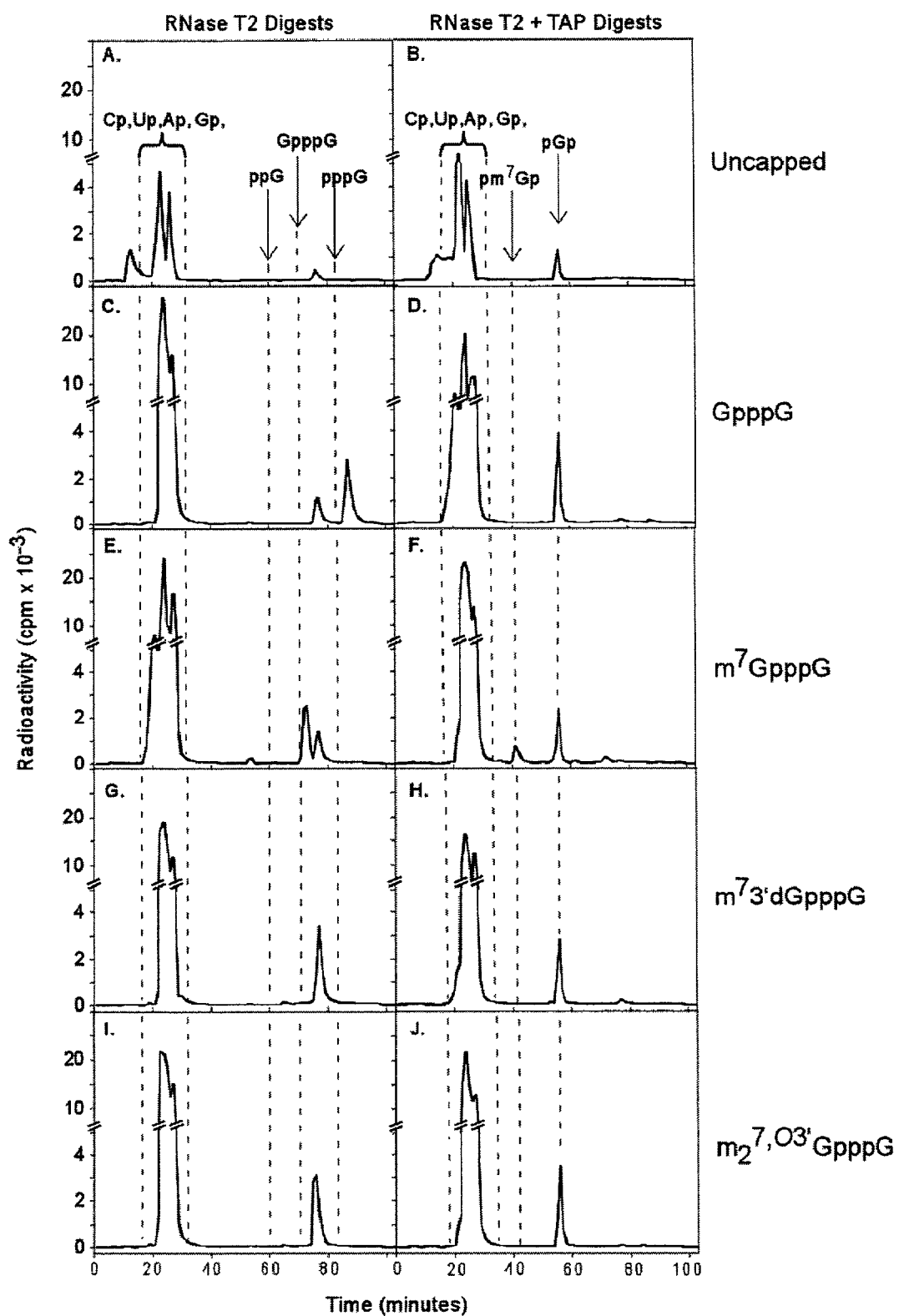
FIG. 2 depicts an analysis of in vitro-synthesized RNAs by enzymatic digestion and anion exchange HPLC.

RNA was synthesized from the short DNA template in the presence of: (1) [α-$^{32}$P]ATP; (2) the other three NTPs (nonradioactive); and (3) either GpppG, m$^7$GpppG, m$^7$3'dGpppG, m$_2$$^{7,O3'}$GpppG, or no cap analogue. The products were digested with RNase T2 and resolved by anion exchange HPLC. FIG. 2 depicts an analysis of the in vitro-synthesized RNAs by enzymatic digestion and anion exchange HPLC. The mRNAs were generated by transcription of NcoI-digested pSP–luc+ with [α-$^{32}$P]ATP and either no cap dinucleotide (panels A, B), GpppG (panels C, D), m$^7$GpppG (panels E, F), m$^7$3'dGpppG (panels G, H), or m$_2$$^{7,O3'}$GpppG (panels I, J). Aliquots of 5 to 13 ng of RNA were digested with RNase T2 (left panels), or with both RNase T2 and TAP (right panels). Nucleotides and caps were separated on a Partisil 10SAX/25 column developed with a gradient of potassium phosphate, pH 3.5. Fractions of 1 mL were collected, and their Cerenkov radiation was determined with a Beckman LS 6500 scintillation counter. The elution times of the following standard compounds, detected by UV absorption, are also shown: 3'-CMP; 3'-UMP; 3'-AMP; 3'-GMP; 5'-GDP; 5'-GTP; 3',5'-GDP (pGp); 3',5'-m$^7$GMP (pm$^7$Gp); and GpppG.

Uncapped RNA yielded primarily 3'-NMPs (Panel A, 20–30 min) with a small amount of material that may have been the partially degraded product ppGp* (Panel A, 76 min). The expected product pppGp* was not observed. Due to its high negative charge, that species may not have eluted from the column. Its presence, however, is likely since RNase T2 plus TAP digestion yielded pGp* (Panel B, 56 min) where none had existed previously (compare Panel A).

TABLE 3

Predicted and observed cap structures from in vitro-synthesized mRNAs after enzymatic digestion

|  |  |  | Possible 5' end labeled digestion products | | Product observed |
| --- | --- | --- | --- | --- | --- |
| Cap dinucleotide | Orientation[1] | Possible transcription products | RNase T2 | RNase T2 + TAP | RNase T2 + TAP |
| None | N/A | pppGP*AP(NP)$_{40}$C | pppGp* | pGp* | 100% |
| GpppG | N/A | GpppGp*Ap(Np)$_{40}$C | GpppGp* | pGp* | 100% |
| m$^7$GpppG | Normal | m$^7$GpppGp*Ap(Np)$_{40}$C | m$^7$GpppGp* | pGp* | 67% |
|  | Reverse | Gpppm$^7$Gp*Ap(Np)$_{40}$C | Gpppm$^7$Gp* | pm$^7$Gp* | 33% |
| m$^7$3'dGpppG | Normal | m$^7$3'dGpppGp*Ap(Np)$_{40}$C | m$^7$3'dGpppGp* | pGp* | 100% |
|  | Reverse | Gpppm$^7$3'dGp*Ap(Np)$_{40}$C | Gpppm$^7$3'dGp* | pm$^7$3'dGp* | 0% |
| m$_2$$^{7, O3'}$GpppG | Normal | m$_2$$^{7, O3'}$GpppGp*Ap(Np)$_{40}$C | m$_2$$^{7, O3'}$GpppGp* | pGp* | 100% |
|  | Reverse | Gpppm$_2$$^{7, O3'}$Gp*Ap(Np)$_{40}$C | Gpppm$_2$$^{7, O3'}$Gp* | pm$^{7, O3'}$Gp* | 0% |

[1]"Normal" orientation means that the 3'-OH of Guo in the structure m$^7$G(5')ppp(5')G (or its analogues) is attached to the first nucleotide residue in the RNA chain by a 3'–5' phosphodiester linkage. "Reverse" orientation means that the 3'-OH of m$^7$Guo is the point of attachment.
[2]Radioactive atoms ($^{32}$P) are indicated by *.

The RNase T2-digestion products of normal and reverse m$^7$GpppG-capped RNAs (M$^7$GpppGp* and Gpppm$^7$Gp*, respectively) have identical masses and charges; they would therefore be expected to elute from an anion exchange column at nearly the same time. However, TAP digestion of normal and reverse-capped mRNAs should yield two alternate labeled products, pGp* and pm$^7$Gp*, that differ in both charge and mass, because the m$^7$ group confers a positive charge on G. The nucleotides pm$^7$3'dGp* and pm$_2$$^{7,O3'}$Gp* have the same charge as pm$^7$Gp*. Thus, although RNase T2 digestion alone would not be expected to distinguish between normal and reverse orientations, the combination of RNase T2 and TAP should do so (see Table 3).

In the case of GpppG-capped RNAS, RNase T2 alone yielded a structure eluting at 89 min (FIG. 2, Panel C), likely GpppGp* (the presence of a second phosphate ester reduces the charge relative to pppGp*). The minor peak at 77 min may have been the partially degraded product ppGp*. Consistent with these assignments, both compounds disappeared following TAP digestion, coinciding with the appearance of a new peak corresponding to pGp* at 56 min (FIG. 2, Panel D). As expected, no pm$^7$Gp* (42 min) was formed.

The major, highly-charged RNase T2-resistant product from m$^7$GpppG-capped RNA eluted at 73 min (FIG. 2, Panel E), likely m$^7$GpppGp*. This compound eluted earlier than the peak at 89 min in Panel C, tentatively assigned the structure GpppGp*, because of the additional positive charge. The minor peak at 77 min may be the reverse cap GPPPm⁷Gp*, suggesting that the proximity of the 3'-P to the positive charge of the m⁷G ring may influence the charge on the P. These assignments are strengthened by the fact that TAP digestion converted these products to two labeled compounds that eluted earlier, pGp* (56 min) and pm⁷Gp* (42 min) (FIG. 2, Panel F). The ratio of pGp* to pm⁷Gp* suggest that they were derived from the 73- and 77-min peaks of Panel E, respectively.

With the ARCA m⁷3'dGpppG, an RNase T2-resistant product was observed at 78 min, likely m⁷3'dGpppGp* (FIG. 2, Panel G). It eluted at nearly the same time as the compound thought to be m⁷GpppGp* (78 min versus 77 min for Panels G and E, respectively). Note that where there were two peaks in this region for RNA synthesized with m⁷GpppG (Panel E), there was only one peak for RNA synthesized with the ARCA (Panel G), consistent with the inability of the ARCA to be incorporated in the reverse orientation. After digestion with TAP, the peak at 78 min disappeared and a new one appeared at the elution time of pGp* (Panel H, 56 min). The fact that no pm⁷Gp* appeared at 42 min with the ARCA (Panel H), while it did with m⁷GpppG (Panel F), is further proof that the ARCA was incorporated in only a single orientation.

The products observed upon digestion of RNA synthesized with the second ARCA, $m_2^{7,O3'}$GpppG (FIG. 2, Panels I and J), eluted almost the same as those that had been obtained with the m⁷3'dGpppG-capped RNA—again, consistent with the expectation that the ARCA should be incorporated in only one orientation.

EXAMPLE 20

Competitive Inhibition of Protein Synthesis by ARCAs

Figure 3:
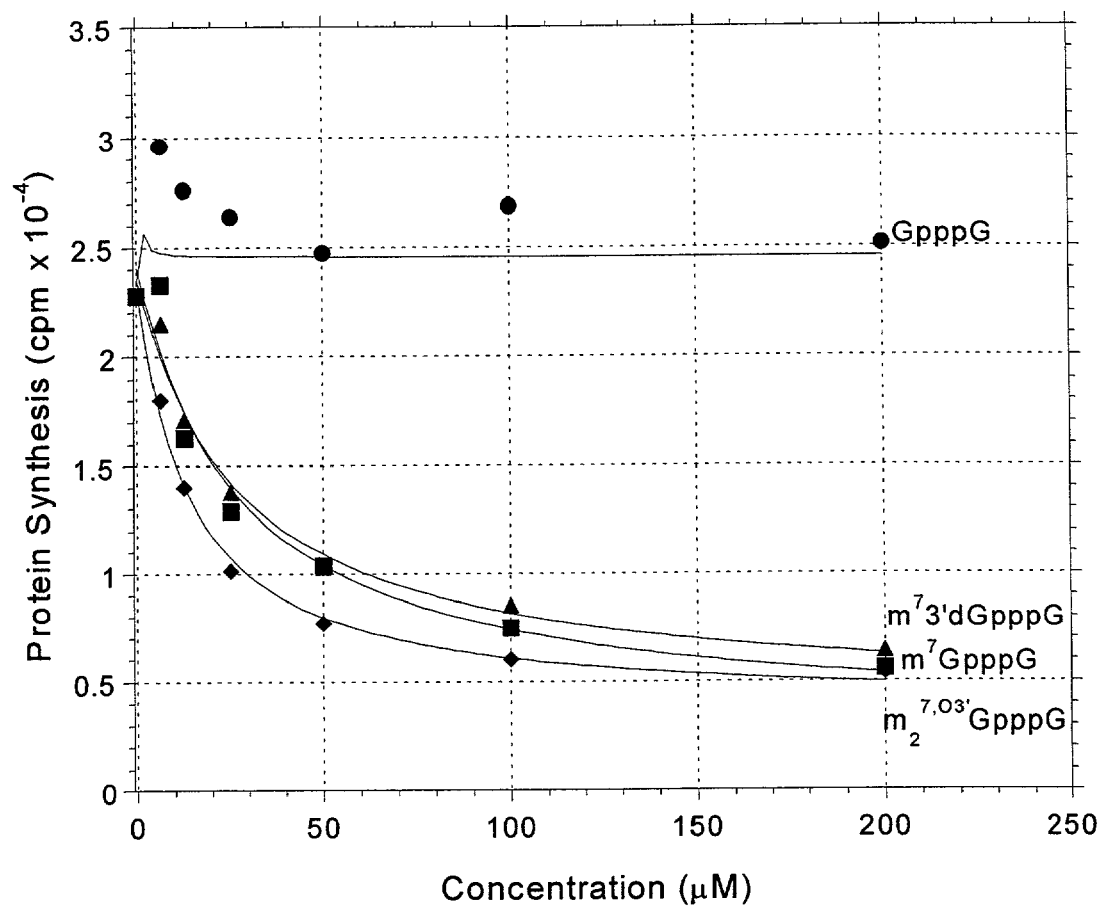
FIG. 3 depicts the inhibition of translation by ARCAs compared with $m^7GpppG$ and GpppG.

One measure of the interaction between a cap analogue and the translational machinery is competitive inhibition of protein synthesis. The binding of cap analogues to eIF4E, measured in vitro with purified components, and the resulting competitive inhibition of protein synthesis in a cell-free translation system have been correlated for several different cap analogue structures. We separately tested GpppG, m⁷GpppG, and the two ARCAs for their ability to compete with natural globin mRNA for recognition by the translational machinery, and thereby to inhibit translation in an RRL system. GpppG did not act as an inhibitor, and in fact slightly stimulated protein synthesis at low concentrations. The two ARCAs, on the other hand, were equally as inhibitory as m⁷GpppG. FIG. 3 depicts the inhibition of translation by ARCAs compared with m⁷GpppG and GpppG. Natural rabbit globin mRNA was translated at 5 µg/mL in the RRL system, and globin synthesis was detected by incorporation of [³H]Leu into protein. The following cap analogues were included during translation at the indicated concentrations: GpppG, circles; m⁷GpppG, squares; m⁷3'dGpppG, triangles; and $m_2^{7,O3'}$GpppG, diamonds.

One may compare cap analogues as inhibitors quantitatively, by fitting a theoretical curve to observed translation data. The value of the dissociation constant, $K_i$, for the cap analogue•eIF4E complex was varied to obtain the best least-squares fit. FIG. 3 depicts such curves for m⁷GpppG, m⁷3'dGpppG, and $m_2^{7,O3'}$GpppG, with corresponding $K_i$ values of 27.8±12.6, 27.8±7.1, and 14.3±1.9 µM, respectively. Although it appeared in this experiment that the $m_2^{7,O3'}$GpppG compound was more inhibitory, in a replicate of this experiment the $K_i$ values for the ARCAs did not differ statistically from those of m⁷GpppG.

EXAMPLE 21

Translation of ARCA-capped mRNAs

Because one-third to one-half of m⁷GpppG was incorporated into RNA in the reverse orientation, because the novel ARCAs were incorporated exclusively in the normal orientation, and because the ARCAs were recognized to the same extent as m⁷GpppG in the translational inhibition experiment, we predicted that a homogeneous population of in vitro-synthesized ARCA-capped mRNAs should be more active translationally than m⁷GpppG-capped mRNAs. We tested this prediction using luciferase mRNAs that were either uncapped, capped with GpppG, capped with m⁷GpppG, or capped with one of the two ARCAs.

Figure 4:
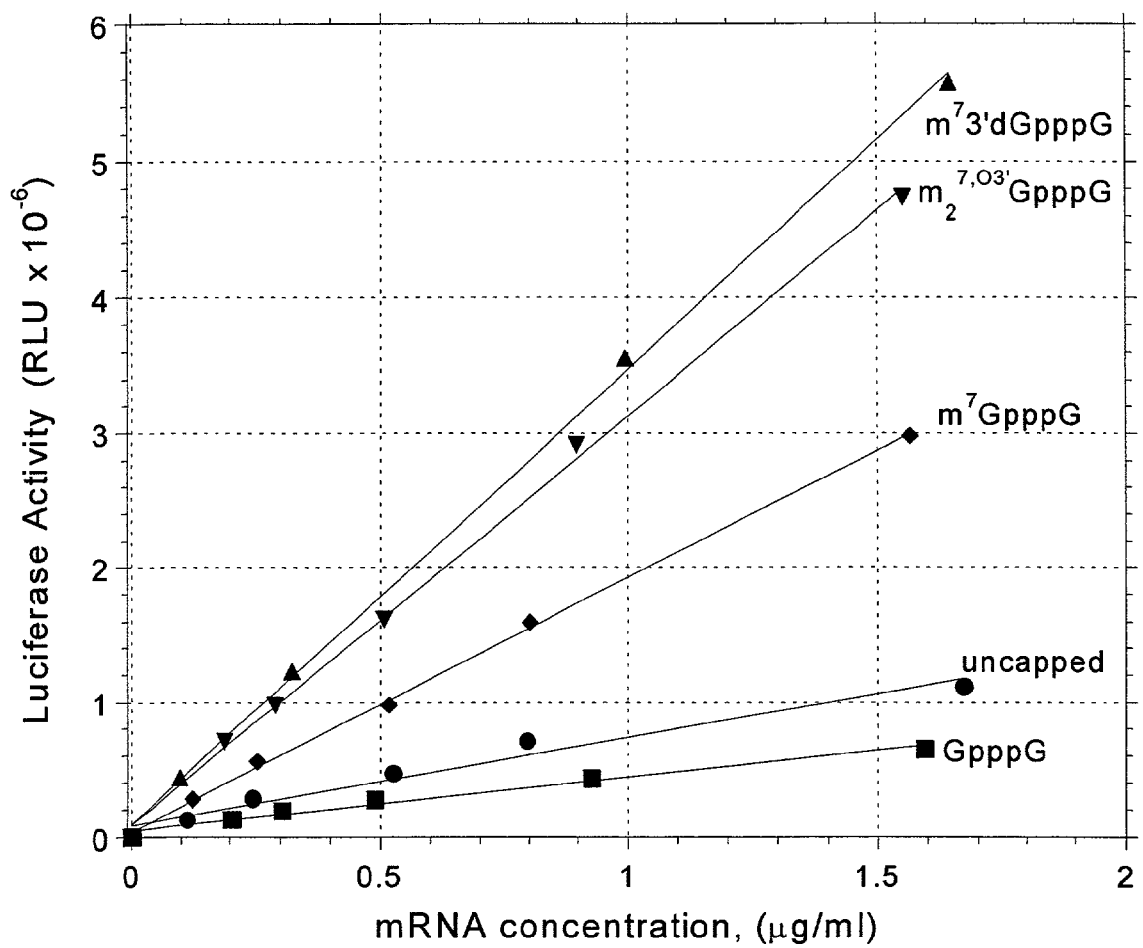
FIG. 4 depicts the translational activity of ARCA-capped mRNAs compared to that of other RNAs.

FIG. 4 depicts the translational activity of the ARCA-capped mRNAs. Luciferase mRNAs were synthesized in vitro using SP6 RNA polymerase in the presence of all four NTPs, and either no cap analogue (circles), GpppG (squares), m⁷GpppG (diamonds), $m_2^{7,O3'}$GpppG (inverted triangles) or m⁷3'dGpppG (triangles). The RNAs were translated for 60 min in the RRL system, and luciferase activity was measured in triplicate by luminometry (RLU, relative light units). Translational efficiency for each mRNA was estimated from the slopes of the curves of luciferase activity versus mRNA concentration.

The fact that all the m⁷G-containing mRNAs were translated more efficiently than the uncapped or GpppG-capped mRNAs indicated that the RRL system we used was highly dependent on the presence of a cap on the mRNA. As shown in FIG. 4, we found that the $m_2^{7,O3'}$GpppG-and m⁷3'dGpppGp-capped mRNAs were more efficient in translation than m⁷GpppG-capped mRNA. In six experiments employing four separate batches of in vitro-synthesized mRNAs, the mRNAs produced with the novel ARCAs were consistently more active than those produced with m⁷GpppG.

Pasquinelli et al. (1995) found that the extent of reverse capping varied between 28% and 48%, depending on the pH of the in vitro-transcription reaction. In the experiments whose results are shown in FIG. 2 and summarized in Table 3, the extent of reverse capping was approximately 33%. Assuming that the novel ARCAs and normal caps stimulate translation to the same degree, an assumption that seems likely based on the inhibition data (FIG. 3), we predicted that the (homogeneous) preparation of ARCA-capped mRNA should be more active than the (heterogeneous) preparation of m⁷GpppG-capped mRNAs, a prediction that was consistent with our experimental observations.

These results showed that the novel ARCAs behaved very similarly to normal cap analogues, except that they were not incorporated into RNAs in the reverse orientation, and that they can cause substantially higher translational activity. The modifications at the 3'-O-position of m⁷Guo did not appear to substantially alter conformation (Table 2) or interaction with translational machinery (FIGS. 3 and 4). The ARCAs have the advantage of being incorporated into RNA exclusively in the normal orientation, but have no apparent disadvantages. To our knowledge, the degree to which m⁷G is incorporated in place of G in internal positions of a synthetic RNA chain by bacteriophage polymerases has not been rigorously determined. Regardless of the level of such misincorporation, the ARCAs should be essentially incapable of donating m⁷G either internally or at the 5'-end. A different type of ARCA, e.g., $m_4^{2,2,7,O3'}$GpppG or $m_3^{2,2,7}$3'dGpppG, would be useful for in vitro synthesis of U-type snRNAs with 100% normal cap orientation.

EXAMPLE 22

An Arabinose-derived ARCA

Anti-reverse mRNA cap analogues may also be derived from arabinose, for example:

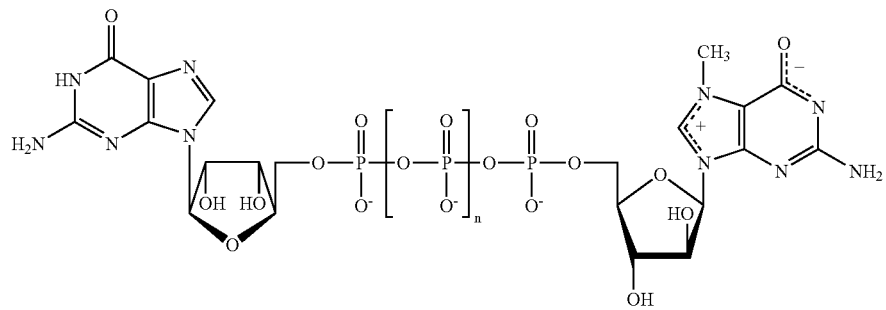

For example, where n=1, this ARCA may be synthesized starting with 9-β-D-arabinofuranosylguanine, which is commercially available or which may be prepared by the method of Ikehara et al., "Studies of nucleosides and nucleotides. XLVIII. Purine cyclonucleosides. 29. A new method for the synthesis of 9-β-arabinofuranosylguanine (Ara G)," *J. Carbohydr. Nucleosides Nucleotides*, vol. 3, pp. 149–159 (1976), in place of the 3'-deoxyguanosine in Example 1.

Although the examples described above employed particular cap analogs, other analogs will also work in practicing the invention, for example:

Note that both 2' and 3' modifications may be used. These compounds may, for example, be synthesized in a manner generally analogous to the syntheses described above. For example, the synthesis of alternative 3 in the above list (X=OCH$_3$, Y=OH, n=1) may be conducted in a manner similar to that described in the above Examples, starting by replacing the 3'-O-methylguanosine with 2'-O-methylguanosine in Example 2, the synthesis of the latter of which is also described in Kusmierek et al. (1978).

Likewise, the synthesis of alternative 4 in the above list (X=H, Y=OH, n=1) may be conducted in a manner similar to that described in the above Examples, starting with 2'-deoxyguanosine 5'-diphosphate, which is commercially available, in Example 3 in lieu of 2'-deoxyguanosine 5'-diphosphate.

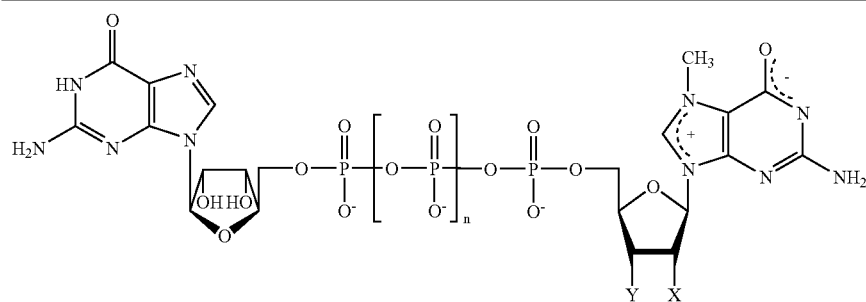

1. m$_2$$^{7,3'O}$GpppG:      X = OH,        Y = OCH$_3$,    n = 1;
2. m$^7$3'dGpppG:             X = OH,        Y = H,          n = 1;
3. m$_2$$^{7,2'O}$GpppG:      X = OCH$_3$,   Y = OH,         n = 1;
4. m$^7$2'dGpppG:             X = H,         Y = OH,         n = 1;
5. m$^7$2',3'didGpppG:        X = H,         Y = H,          n = 1;
6. m$_3$$^{7,2'O, 3'O}$GpppG: X = OCH$_3$,   Y = OCH$_3$,    n = 1;
7. m$^7$et$^{3'O}$GpppG:      X = OH,        Y = OC$_2$H$_5$, n = 1;
8. m$^7$et$^{2'O}$GpppG:      X = OC$_2$H$_5$, Y = OH,       n = 1;
9. m$_2$$^{7,3'O}$GppppG:     X = OH,        Y = OCH$_3$,    n = 2;
10. m$^7$3'dGppppG:           X = OH,        Y = H,          n = 2;
11. m$_2$$^{7,2'O}$GppppG:    X = OCH$_3$,   Y = OH,         n = 2;
12. m$^7$2'dGppppG:           X = H,         Y = OH,         n = 2;
13. m$^7$2',3'didGppppG:      X = H,         Y = H,          n = 2;
14. m$_3$$^{7,2'O, 3'O}$GppppG: X = OCH$_3$, Y = OCH$_3$,    n = 2;
15. m$^7$et$^{3'O}$GppppG:    X = OH,        Y = OC$_2$H$_5$, n = 2;
16. m$^7$et$^{2'O}$GppppG:    X = OC$_2$H$_5$, Y = OH,       n = 2.

The synthesis of alternative 5 may be conducted in a similar manner, starting with 2',3'-dideoxyguanosine (which is commercially available) in lieu of 3'-deoxyguanosine in Example 1.

The synthesis of alternative 6 may be conducted by modifying the procedure of Kusmierek et al. (1978) by using a large excess of methylation reagent to prepare the starting material to use as otherwise described in the Examples, starting with Example 2.

The synthesis of alternative 7 may be conducted by modifying the procedure of Kusmierek et al. (1978) by using diazoethane (instead of diazomethane) as alkylating reagent to prepare the starting material to use as otherwise described in the Examples, starting with Example 2.

The synthesis of alternative 8 may be conducted by modifying the procedure of Kusmierek et al. (1978) by using diazoethane (instead of diazomethane) as alkylating reagent to prepare the starting material to use as otherwise described in the Examples, starting with Example 2.

The synthesis of alternatives 9–16 (n=2) may be conducted as otherwise described in the above Examples, or in the above syntheses of alternatives 3–8 (n=1), as appropriate, but using GDP instead of GMP in the steps as otherwise described in Example 7. Likewise, analogues with higher values of n may be prepared using guanosine triphosphate, guanosine tetraphosphate, guanosine pentaphosphate, etc. in lieu of GMP in the steps otherwise described in Example 7.

We expect that 2',3'-dideoxy- and 2',3'-dimethyl cap analogs will function in the present invention. We also expect that introducing additional phosphate groups into the phosphate bridge (creating, e.g., dinucleotide tetraphosphates or even penta-, hexa-, or heptaphosphates (n=3, 4, or 5 in the above structure))—will produce compounds that may be more effective than the triphosphates. Other possible substituents X and Y include $OCH_2CH_3$. If Y is OH, then it is preferred that X is neither H nor OH.

The "non-methylated" guanosine in the ARCA may be replaced with another nucleoside, e.g., uridine, adenosine, or cytosine:

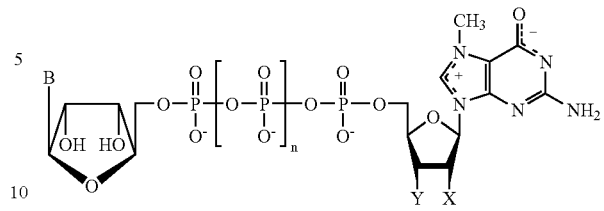

wherein the moiety B is selected from the group consisting of

B:

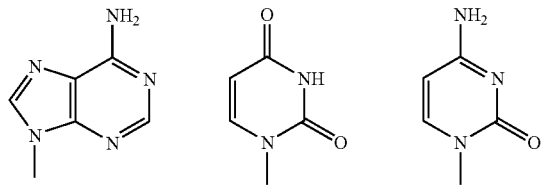

The synthesis of the ARCAs with these alternative nucleosides may be conducted as otherwise described in the above Examples, or in the above syntheses of alternatives 1–16, as appropriate, but using AMP, ADP, ATP, UMP, UDP, UTP, CMP, CDP, CTP, etc. in lieu of GMP in the steps otherwise described in Example 7.

Another alternative is to replace the 7-methyl group with another substituent, such as $C_1$ to $C_4$ substituted or unsubstituted alkyl, $C_6$ to $C_8$ substituted or unsubstituted aryl, or $C_1$ to $C_4$ substituted or unsubstituted alkoxy, as illustrated in the examples below:

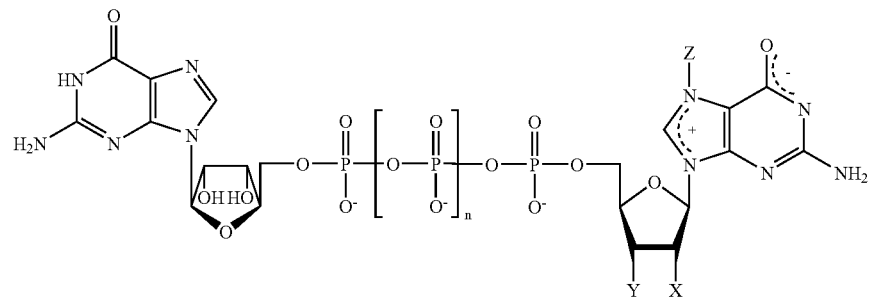

| | | | | |
|---|---|---|---|---|
| [a] et[7]m[3'O]GpppG: | X = OH, | Y = $OCH_3$, | Z = $C_2H_5$ | n = 1; |
| [b] et[7]3'dGpppG: | X = OH, | Y = H, | Z = $C_2H_5$ | n = 1; |
| [c] bn[7]m[3'O]GpppG: | X = OH, | Y = $OCH_3$, | Z = $CH_2C_6H_5$ | n = 1; |
| [d] bn[7]3'dGpppG: | X = OH, | Y = H, | Z = $CH_2C_6H_5$ | n = 1; |
| [e] et[7]m[3'O]GpppG: | X = OH, | Y = $OCH_3$, | Z = $C_2H_5$ | n = 2; |
| [f] et[7]3'dGpppG: | X = OH, | Y = H, | Z = $C_2H_5$ | n = 2; |
| [g] bn[7]m[3'O]GpppG: | X = OH, | Y = $OCH_3$, | Z = $CH_2C_6H_5$ | n = 2; |
| [h] bn[7]3'dGpppG: | X = OH, | Y = H, | Z = $CH_2C_6H_5$ | n = 2; |
| [i] pFbn[7]m[3'O]GpppG: | X = OH, | Y = $OCH_3$, | Z = $CH_2C_6H_4pF$ | n = 1; |
| [j] pFbn[7]3'dGpppG: | X = OH, | Y = H, | Z = $CH_2C_6H_4pF$ | n = 1; |
| [k] pClbn[7]m[3'O]GpppG: | X = OH, | Y = $OCH_3$, | Z = $CH_2C_6H_4pCl$ | n = 1; |
| [l] pClbn[7]3'dGpppG: | X = OH, | Y = H, | Z = $CH_2C_6H_4pCl$ | n = 1; |
| [m] pFbn[7]m[3'O]GpppG: | X = OH, | Y = $OCH_3$, | Z = $CH_2C_6H_4pF$ | n = 2; |

-continued

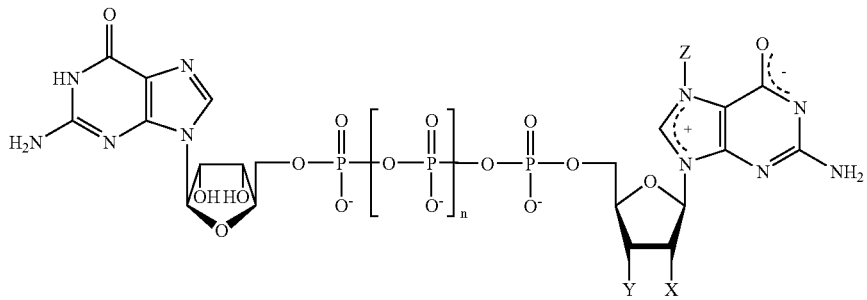

| | | | | | |
|---|---|---|---|---|---|
| [n] pFbn⁷3'dGpppG: | X = OH, | Y = H, | Z = CH$_2$C$_6$H$_4$pF | n = 2; |
| [o] pClbn⁷m³'ᴼGpppG: | X = OH, | Y = OCH$_3$, | Z = CH$_2$C$_6$H$_4$pCl | n = 2; |
| [p] pClbn⁷3'dGpppG: | X = OH, | Y = H, | Z = CH$_2$C$_6$H$_4$pCl | n = 2; |

The synthesis of alternatives [a] and [b] above may be carried out, for example, as otherwise described in the Examples above, starting with Example 5 or 6, and replacing the 100 μL of methyl iodide with 100 μL of ethyl iodide.

The synthesis of alternatives [c] and [d] above may be carried out, for example, as otherwise described in the Examples above, starting with Example 5 or 6, and replacing the 100 μL of methyl iodide with 100 μL of benzyl bromide. See generally M. Jankowska et al., "Synthesis and properties of new NH$_2$ and N7 substituted GMP and GTP 5'-mRNA cap analogues," *Collect Czech. Chem. Commun.*, vol. 58, pp. S138–S141 (1993).

The synthesis of alternatives [e] through [h] above may be carried out, for example, as otherwise described in the Examples above, starting with Examples 5 through 8, and replacing the 100 μL of methyl iodide with 100 μL of ethyl iodide or benzyl bromide, as appropriate, and replacing GMP with GDP.

The synthesis of alternatives [i] through [p] above may be carried out, for example, as otherwise described in the Examples above, starting with Examples 5 through 8, and replacing the 100 μL of methyl iodide with 100 μL of p-chlorobenzyl chloride or p-fluorobenzyl chloride, as appropriate, and replacing GMP with GDP when appropriate. See Jankowska et al. (1993).

Another possible modification is a methyl or other substitution at the N² position:

where, R may, for example, be H, CH$_3$, CH$_2$C$_6$H$_5$, CH$_2$COC$_6$H$_5$, CH$_2$CH$_2$CH$_2$OH, CH$_2$CH=CH$_2$, or another substituent, such as C$_1$ to C$_4$ substituted or unsubstituted alkyl, or C6 to C$_8$ substituted or unsubstituted aryl. Such modifications may, for example, be made at the beginning of the synthetic route, in the initial synthesis of the nucleoside, prior to carrying out the other steps of the synthesis. For example, N²,3'-O-dimethylguanosine 5'-monophosphate may be obtained by a procedure analogous to that for Compound 3, but instead starting with N²,3'-O-dimethylguanosine, which may be prepared by introduction at the beginning of methyl groups into the N² position of guanosine by the method of J. Boryski et al., *Nucleosides Nucleotides*, vol. 4, pp. 595 ff (1985); or Sekine et al., "A convenient method for the synthesis of N²,N²-dimethylguanosine by reductive C—S bond cleavage with tributyltin hydride," *J. Org. Chem.*, vol.56, pp.1224–1227(1991) See also J. Boryski, "Application of the 1,N-2-isopropenoguanosine system for synthesis of novel N-2-substituted derivatives of guanosine and acyclovir," *Coll. Czech. Chem. Commun.*, vol. 55 (special issue), pp. 85–88 (1990).

Still more generally, compounds in accordance with the present invention will the following:

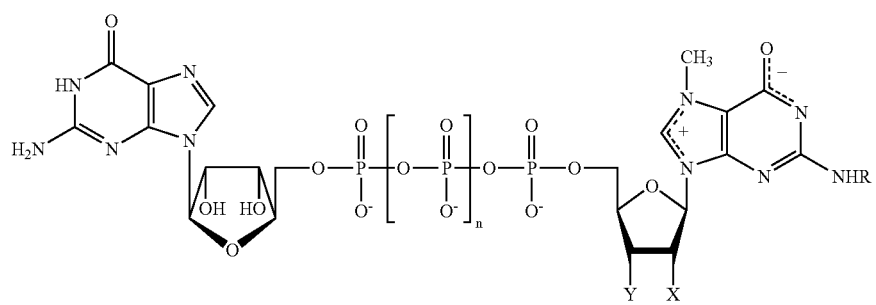

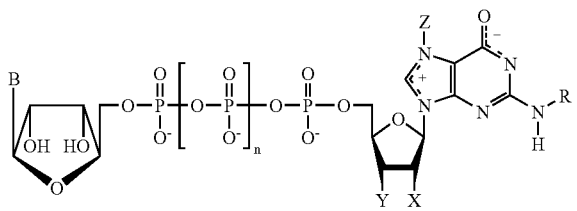

wherein the substituents R, X, Y, and Z are as previously described, and the moiety B is selected from the group consisting of

B:

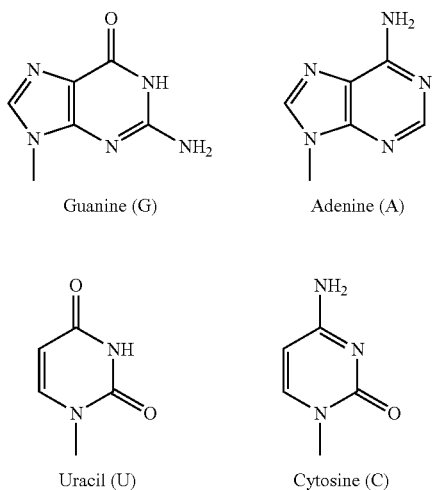

MISCELLANEOUS

The complete disclosures of all references cited in this specification are hereby incorporated by reference. Also incorporated by reference are the complete disclosures of the following publications of the inventors' own work, which are not prior art to the present application: J. Stepinski et al., "Synthesis and properties of mRNAs containing the novel 'anti-reverse' cap analogs 7-methyl(3'-O-methyl)GpppG and 7-methyl(3'-deoxy)GpppG," RNA, vol. 7, pp. 1486–1495 (2001); E. Darzynkiewicz et al., "New 'anti-reverse' 5'-mRNA dinucleotide cap analogues (ARCA)," Abstract POTH-035, 27th Meeting of the Federation of European Biochemical Societies (Lisbon, Portugal, Jun. 30–Jul. 5, 2001); J. Stepinski et al., "Synthesis and properties of 'anti-reverse' cap analogues," Abstract, 6th Meeting of the RNA Society (Banff, Canada, May 29–Jun. 3, 2001); and J. Stepinski et al., "Preparation and properties of mRNAs capped with the novel 'anti-reverse' dinucleotide cap analogues," Abstract P-13, 4th West Coast Meeting on mRNA Stability and Translation (Seattle, Wash., Oct. 14–16, 2001). In the event of an otherwise irreconcilable conflict, however, the present specification shall control.

We claim:

1. A composition comprising

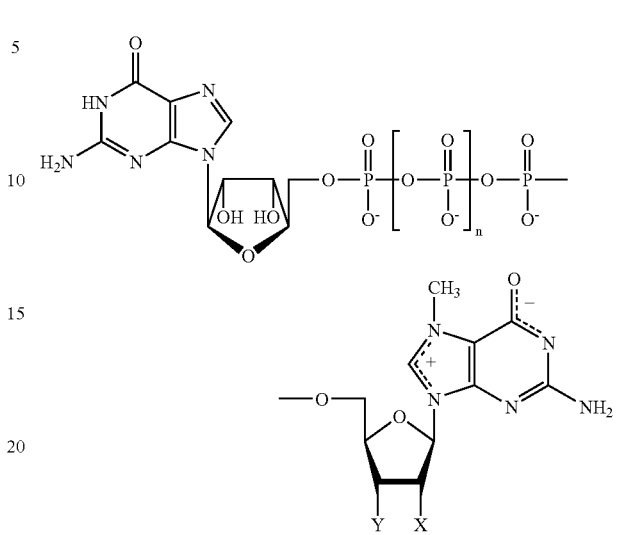

wherein:
X is selected from the group consisting of H, OH, OCH$_3$, and OCH$_2$CH$_3$;
Y is selected from the group consisting of H, OH, OCH$_3$, and OCH$_2$CH$_3$;
and n is, 2, 3, 4, or 5;
and wherein, if Y is OH and n is 1, then X is neither H nor OH.

2. A composition as recited in claim 1, wherein X is OH, Y is H, and n is 1.

3. A composition as recited in claim 1, wherein X is OH, Y is OCH$_3$, and n is 1.

4. An RNA molecule whose 5' end incorporates a composition as recited in claim 1.

5. An RNA molecule whose 5' end incorporates a composition as recited in claim 2.

6. An RNA molecule whose 5' end incorporates a composition as recited in claim 3.

7. A method for synthesizing an RNA molecule as recited in claim 4 in vitro; said method comprising reacting ATP, CTP, UTP, GTP, a composition as recited, and a polynucleotide template; in the presence an RNA polymerase; under conditions conducive to transcription by the RNA polymerase of the polynucleotide template into an RNA copy; whereby some of the RNA copies will incorporate the composition as recited to make an RNA molecule as recited.

8. A method for synthesizing an RNA molecule as recited in claim 5 in vitro; said method comprising reacting ATP, CTP, UTP, GTP, a composition as recited, and a polynucleotide template; in the presence an RNA polymerase; under conditions conducive to transcription by the RNA polymerase of the polynucleotide template into an RNA copy; whereby some of the RNA copies will incorporate the composition as recited to make an RNA molecule as recited.

9. A method for synthesizing an RNA molecule as recited in claim 6 in vitro; said method comprising reacting ATP, CTP, UTP, GTP, a composition as recited, and a polynucleotide template; in the presence an RNA polymerase; under conditions conducive to transcription by the RNA polymerase of the polynucleotide template into an RNA copy; whereby some of the RNA copies will incorporate the composition as recited to make an RNA molecule as recited.

10. A method for synthesizing a protein or a peptide in vitro, said method comprising translating an RNA molecule as recited in claim 4 in a cell-free protein synthesis system, wherein the RNA molecule comprises an open reading frame, under conditions conducive to translating the open reading frame of the RNA molecule into the protein or peptide encoded by the open reading frame.

11. A method for synthesizing a protein or a peptide in vitro, said method comprising translating an RNA molecule as recited in claim 5 in a cell-free protein synthesis system, wherein the RNA molecule comprises an open reading frame, under conditions conducive to translating the open reading frame of the RNA molecule into the protein or peptide encoded by the open reading frame.

12. A method for synthesizing a protein or a peptide in vitro, said method comprising translating an RNA molecule as recited in claim 6 in a cell-free protein synthesis system, wherein the RNA molecule comprises an open reading frame, under conditions conducive to translating the open reading frame of the RNA molecule into the protein or peptide encoded by the open reading frame.

* * * * *